United States Patent [19]

Vestal

[11] Patent Number: 4,883,958

[45] Date of Patent: Nov. 28, 1989

[54] INTERFACE FOR COUPLING LIQUID CHROMATOGRAPHY TO SOLID OR GAS PHASE DETECTORS

[75] Inventor: Marvin L. Vestal, Houston, Tex.

[73] Assignee: 501 Vestec Corporation, Houston, Tex.

[21] Appl. No.: 285,516

[22] Filed: Dec. 16, 1988

[51] Int. Cl.$^4$ ............................................. H01J 41/04
[52] U.S. Cl. ................................... 250/288; 250/281; 250/282
[58] Field of Search ............ 250/281, 282, 288, 288 A

[56] References Cited

U.S. PATENT DOCUMENTS

| | | | |
|---|---|---|---|
| 4,055,987 | 11/1977 | McFadden | 73/61.1 |
| 4,112,297 | 9/1978 | Miyagi et al. | 250/281 |
| 4,298,795 | 11/1981 | Takeuchi et al. | 250/282 |
| 4,403,147 | 9/1983 | Melera et al. | 250/281 |
| 4,531,056 | 7/1985 | Labowsky et al. | 250/281 |
| 4,629,478 | 12/1986 | Browner et al. | 250/288 |
| 4,647,772 | 3/1987 | Lewis et al. | 250/281 |
| 4,730,111 | 3/1988 | Vestal | 250/288 |
| 4,731,533 | 3/1988 | Vestal | 250/292 |
| 4,766,312 | 8/1988 | Fergusson et al. | 250/281 |
| 4,791,292 | 12/1988 | Cooks et al. | 250/288 |
| 4,814,612 | 3/1989 | Vestal et al. | 250/282 |
| 4,820,648 | 4/1989 | Caprioli et al. | 250/288 |

FOREIGN PATENT DOCUMENTS

| | | | |
|---|---|---|---|
| 0102553 | 5/1986 | Japan | 250/281 |
| 61-107156 | 5/1986 | Japan | 250/281 |

OTHER PUBLICATIONS

"Monodisperse Aerosol Generation Interface for Combining Liquid Chromatography with Mass Spectroscopy", Willoughby et al., School of Chemistry, Georgia.
"Improvements in a Particle Beam LC/MS Interface", Apffel, et al., 6/88, 36th ASMS Conference on Mass Spectrometry and Allied Topics.
"Positive-and Negative-Ion Chemical Ionization Mass Spectrometry of Aldicarb and its Derivatives by Particle Beam HPLC/MS", Lynn, et al., 6/88, 36th ASMS Conf.
"Analysis of Drugs of Abuse by Particle Beam LC/MS", Apffel et al., 6/88, 36th ASMS Conference on Mass Spectrometry and Allied Topics.
"LSMIS of Intact Oligosaccharides: Comparison of Sensitivity and Spectral Quality Among Selected Derivatives", Poulter et al., 6/88, 36th ASMS Conference.
"Studies of Anabolic Steroids by Thermabeam LC/MS", Dilts et al., 6/88, 36th ASMS Conference on Mass Spectrometry and Allied Topics.
"Electron Impact Ionization Mass Spectra of Polystyrene Oligomers by Thermabeam LC/MS", Jones, 6/88, 36th ASMS Conference on Mass Spectrometry and Allied.

(List continued on next page.)

Primary Examiner—Carolyn E. Fields
Assistant Examiner—John A. Miller
Attorney, Agent, or Firm—Browning, Bushman, Zamecki & Anderson

[57] ABSTRACT

Improved techniques are provided for interfacing liquid chromatography with gas phase and solid phase detectors. Heated liquid effluent including sample solute of interest and solvent is sprayed into a desolvation chamber, where controlled vaporization of the solvent occurs while maintaining sample particles of interest. A carrier gas is added to the desolvation chamber, and the discharged aerosol is transmitted through a uniform cross-sectional flow path to a condenser, gas diffusion cell, or other solvent removal device. Substantially all transmitted solvent is thereby removed, with the carrier gas and substantially all of the sample particles of interest passing to the detector for analysis. The interface of the present invention is applicable to thermospray technology and other spraying techniques resulting in vaporization and nebulization of the LC effluent. The methods and apparatus of the present invention may be reliably employed with various gas phase or solid phase detectors for sample analysis, and may be used over a wide range of chromatographic conditions.

54 Claims, 4 Drawing Sheets

OTHER PUBLICATIONS

"Secondary Ion Mass Spectrometry of Solute Particle Beams by Thermabeam LC/MS", Willoughby et al., 36th ASMS Conference on Mass Spectrometry and Allied Topics.

"Polymeric Fluorenyl Reagent for the Derivatization of Polyamines in Biological Fluids", Chou et al., Abstract No. 247.

"Supercritical Fluid Chromatographic/Mass Spectrometric Studies of Environmental Samples", Games et al., Abstract No. 248.

"MAGIC: Basic Studies in Transport and Transport Efficiency", Kirk et al., Abstract No. 249.

"Chromatographic Performance and Applications of the MAGIC LC/MS Interface", Harris et al., Abstract No. 250.

"Ion Spray LC/MS Determination of Neuro Peptides with Atmospheric Pressure Ionization", Lee et al., Abstract No. 251.

"Comparison of Different Absorbance Detection Techniques LC-UV-MS", Dourdeville et al., Abstract No. 252.

"An Improved Thermospray LC/C1/E1 Ion Source for Structural Elucidation in Combined Liquid Chromatography/Mass Spectrometry", Vestal et al., Abst. No. 253.

"Electron Impact Mass Spectra with Thermabeam LC/MS", Willoughby et al., Abstract No. 255.

"Design of a New Liquid Chromatographic System for LC-UV-MS", Cassis et al., Abstract No. 256.

"Integrated Thermospray and Thermabeam Sample Introduction for LC/MS and SFC/MS", Buchner, Abstract No. 257.

"Revenants in Chemical Analysis", Lodder et al., Abstract No. 258.

"Particle Concentration Fluorescence Immunoassay for Tissue Plasminogen Activator", Sportsman et al., Abstract No. 329.

"Structural Elucidation in Biomedical and Pharmaceutical Analysis via Mass Spectroscopy Using Thermabeam and Thermaspray LC/MS", Sheehan, Abstract #330.

"Legally Defensible Data on Drugs of Abuse by Thermabeam LC/MS", Pizzitola et al., Abstract No. 668.

"Evaluation of Thermospray Liquid Chromatography-Mass Spectrometry for Drugs of Abuse", Vestal, Abstract No. 669.

"Determination of Spent Solvent Wastes in Water By Thermospray Liquid Chromatography-Mass Spectrometry", Vestal, Abstract No. 1260.

"New Ways to Get Excited with LC/MS and Environmentally Significant Compounds", Pizzitola et al., Abstract No. 1261.

"Solid Phase Extraction for Determination of Urea and Carbamate Pesticides in Ground Water", Englel et al., Abstract No. 1337.

"Particle Beam Liquid Chromatography Mass Spectrometry (PB/LC/MS): A New Technique Applied to Determinations of Environmental, Forensic and Defense Interest", Sauter et al., Abstract No. 759.

"Fundamental Studies of High Efficiency Sputtering System for Atomic Spectroscopy", Piepmeier et al., Abstract No. 760.

"Capillary Diameter Effects on Thermospray Sample Introduction to ICP-AES", Koropchak et al., 1/88, Winter Conference on Plasma Spectrochemical Analysis.

"Thermospray Interfacing for Flow Injection Analysis with Inductively Coupled Plasma Atomic Emission Spectrometry", Koropchak et al., 4/86.

"A Comparison Between Thermospray and Particle Beam LC/MS for Environmental Applications", Apffel et al., 7/88, Symposium on Waste Testing & Quality Assurance.

INTERFACE FOR COUPLING LIQUID CHROMATOGRAPHY TO SOLID OR GAS PHASE DETECTORS

BACKGROUND OF THE INVENTION

1. Field of the Invention

The present invention relates to devices which interface between liquid chromatographic units and gas phase or solid phase detectors and, more particularly, relates to an improved interface which utilizes controlled partial vaporization and nebulization of the liquid effluent to transport the sample as an aerosol while efficiently removing most of the solvent vapors.

2. Description of the Prior Art

The detection of effluent from chromatographic devices has been applied to almost all areas of science requiring chemical analysis. Such detectors usually involve the measurement of either (1) a bulk property of the effluent (such as the refractive index) which is sensitive to the presence of the sample, (2) a property of the sample not possessed by the mobile phase (such as optical density at a suitable wavelength), or (3) a property of the sample after elimination of the mobile phase.

In gas chromatography (GC), the properties of the samples of interest are often sufficiently different from suitable mobile phases, and accordingly the second approach can generally be used with negligible interference. The analytical power of gas chromatography is thus widely recognized, despite the fact that less than 20% of known organic compounds are suitable for GC without chemical derivatization. Part of this power stems from the wide variety of detectors which are available for routine use with gas chromatography, such as flame ionization, photoionization, ICP, FTIR, flame photometric, thermal conductivity, and mass spectrometry. Certain of these detectors, e.g. flame ionization, are almost universal, i.e. can be reliably used for analysis of a wide range of GC samples.

In liquid chromatography (LC), the properties of the sample in the mobile phases are often similar to those of the mobile phase itself. An almost universal LC detector comparable to flame ionization for GC does not currently exist. Accordingly, reliable detection of LC samples has generally been obtained using equipment specially designed for limited purposes. While LC is applicable to a much broader range of samples than GC, its limited utility is thus partially attributable to the lack of a suitable universal LC detector.

Tremendous advances have been made during the past two decades in LC technology, particularly with respect to high-performance liquid chromatography (HPLC) column technology, and in the development of improved instrumentation to monitor LC effluent to detect, quantify, and preferably identify the eluting components. Probably the most widely used detectors for use with HPLC are photometers, which are based on ultraviolet or visible light absorption differences. While photometers have high sensitivity for many solutes, samples must absorb in the spectral region where the mobile phase is essentially transparent (typically 200 to 600 nm). Those skilled in the art have long recognized that this restricted spectral region is a serious limitation of photometric detectors, since the strongest optical absorption bands occur for most samples and mobile phases at shorter wavelengths.

The thermospray technique was developed primarily for coupling liquid chromatography to a particular gas phase detector, namely mass spectrometry. Thermospray technology provides an LC to mass spectrometry interface which has significant advantages compared to other coupling techniques. In thermospray technology, the LC effluent is partially vaporized and nebulized in a heated vaporizer probe to produce a supersonic jet of vapor containing a mist of fine droplets or particles. As the droplets or particles travel at a high velocity through the heated ion source, they continue to vaporize due to rapid heat input from the surrounding hot vapor. Thermospray thus employs controlled heating of the capillary and the ion source to convert the LC liquid stream into gas phase ions for introduction into the mass spectrometer. A more detailed description of the major components and function of the thermospray system are disclosed in U.S. Pat. No. 4,730,111.

A significant disadvantage of thermospray, as well as other direct coupling techniques between liquid chromatographic devices and mass spectrometers, is that ionization occurs in a bath of solvent vapor at a relatively high source pressure (typically 1 torr or more). This pressure effectively precludes the use of electron impact (EI) ionization, and also limits the choice of reagents in chemical ionization (CI). Moreover, detection utilizing thermospray interface technology has heretofore been limited to a fairly narrow range of chromatographic conditions, since thermospray ionization performs best when the solvent flow rate is in excess of 1 mL/minute, and at least 20% of the mobile phase is water.

Various attempts have been made to overcome the limitations of interfaces between liquid chromatographic units and detectors. One commercially successful technique is similar to that described in U.S. Pat. No. 4,055,987. This technique unfortunately involves various moving wires and belts, and accordingly has significant operational drawbacks which have become widely recognized by those skilled in the art.

A second type of liquid chromatography to gas phase detector interface is known by the acronym MAGIC, which stands for Monodisperse Aerosol Generation Interface for Chromatography. In this device, the LC effluent is forced under pressure through a relatively small orifice (typically 5 to 10 microns in diameter, such that the liquid jet breaks up into a stream of relatively uniform droplets as a result of Rayleigh instability. A short distance downstream, the stream of particles is intersected at 90° by a high velocity gas stream (usually helium) to disperse the particles and prevent coagulation. The dispersed droplets proceed at a relatively high velocity through a desolvation chamber, where vaporization occurs at atmospheric pressure and near ambient temperature. Heating is input to the desolvation chamber to replace the latent heat of vaporization necessary for solvent evaporation, while not raising the aerosol temperature above ambient. Ideally all the solvent is vaporized, and the sample remains as a solid particle or a less volatile liquid droplet. Further details regarding the MAGIC approach are disclosed in an article by Willoughby and Browner published in 1984 in ANALYTICAL CHEMISTRY, Vol. 56, commencing at page 2626, and in U.S. Pat. No. 4,629,478.

A modified version of a particle beam interface between liquid chromatography and mass spectrometry is disclosed in a series of recently published articles. This technique, referred to as Thermabeam LC/MS, uses a nebulizer which may be similar to a thermospray vaporizer. The interface includes a nebulization stage, an expansion stage, and a momentum separation stage, each axially connected in series. In both the MAGIC and the Thermabeam LC/MS devices, some of the carrier gas and some of the solvent vapor is removed in the momentum separator, but no carrier gas or solvent vapor is removed from the desolvation chamber.

While both the second and third types of interfaces described above apparently produce EI spectra in good agreement with library spectra using sample injections of 100 ng or more, these spectra do not include the low mass region where solvent interference may be expected. Accordingly, it is difficult to determine or evaluate the solvent removal efficiency actually achieved by these techniques. Moreover, improved techniques are required to improve sensitivity for gas phase detectors supplied with effluent from LC and HPLC equipment, and to enable the detectors to be utilized over a broader range of chromatographic conditions. Finally, an improved interface is required which will allow LC effluent to be transmitted for analysis to various types of gas phase detectors, so that the flexibility and versatility of the interface is enhanced and its costs minimized.

The disadvantages of the prior art are overcome by the present invention, and improved methods and apparatus are hereinafter disclosed which provide an interface for coupling liquid chromatography to various types of gas phase detectors.

SUMMARY OF THE INVENTION

The interface of the present invention may be used with various types of gas phase and solid phase detectors, and provides a substantially universal solution to detection of LC effluent. The LC solvent is vaporized and the solvent vapor is efficiently removed, and substantially all samples (except perhaps the most volatile) may be transferred as a particle beam and merged with a carrier gas selected for the particular detector. Pyrolysis and other uncontrolled chemical modifications of the sample may be precluded during this process, and thus thermally labile and nonvolatile components may be readily analyzed by an appropriate detector. The techniques of the present invention are applicable to a wide range of LC flow rates, and essentially all LC mobile phases (even those containing nonvolatile buffers) may be used with the interface of the present invention provided that the introduction of the nonvolatile material can be accommodated by the particular gas phase detector employed.

In a suitable embodiment of the present invention, the interface includes a thermospray vaporizer in which most but not all of the solvent is vaporized, while the remaining unvaporized material is carried along as an aerosol in the high velocity vapor jet. The thermospray jet is introduced into a desolvation chamber, which may be controllably heated to further vaporize the droplets in the aerosol. A carrier gas is added to the desolvation chamber to maintain the desired pressure and flow rate, while the heat input to the thermospray vaporizer and to the desolvation chamber is adjusted so that substantially all of the solvent is vaporized while most of the less volatile materials will be retained in the unvaporized particles. The aerosol then passes through one or more solvent removal chambers, where most if not substantially all of the solvent vapor is removed, either by condensation or by allowing it to diffuse through a membrane to a second counterflowing gas stream. The resulting dry aerosol may then be transmitted to a suitable detector, either directly or through a particle beam momentum separator to increase the concentration of particles relative to the remaining solvent vapor and carrier gas.

The flow path through the solvent removal chamber(s) preferably has a substantially uniform cross-sectional area, such that rapid expansion or contraction of the fluid stream is minimized, and "dead spaces" are eliminated. A series of such chambers may be provided, with each chamber removing a portion of the solvent vapor. The solvent is preferably removed from the aerosol of unvaporized sample particles and inert carrier gas in a counterflow process, thereby enabling continuous operation of the system from the LC to the gas phase detectors. Since the interface allows most of the solvent to be removed while the sample is retained and transmitted as an aerosol, several significant advantages are obtained. When used with a particle beam momentum separator to further reduce the pressure of vapor and carrier gas transmitted along with the particles in the aerosol, the technique of the present invention is particularly well suited for use with both EI (electron impact) and CI (chemical ionization) mass spectrometry. Limitations imposed by the transmission of large amounts of solvent vapor in conventional approaches are obviated by the present invention. Also, significant service problems frequently associated with the vacuum pumps used with particle beam separators or conventional thermospray systems are avoided, since in the present invention the vapor load on the vacuum pumps is substantially reduced.

It is an object of the present invention to provide an improved interface for transmitting samples contained in an LC effluent to a gas phase or solid phase detector.

It is a further object of the present invention to provide an interface which provides an improved signal to noise ratio output from the detector compared to conventional prior art techniques by substantially reducing the amount of solvent transported to the detector.

It is a feature of the present invention to provide an LC to gas phase detector interface which utilizes at least one chamber for removing solvent vapor, with the chamber having a substantial uniform cross-sectional gas flow area.

It is another feature of the present invention that the interface is applicable to thermospray technology, so that the controlled partial vaporization of the gas from the thermospray capillary may occur, with further vaporization occurring in the desolvation chamber downstream from the capillary.

It is a further feature of the present invention that the interface may include a plurality of solvent removal chambers connected in series for continuously removing solvent vapor from the stream and supplying substantially dry particles to the gas phase detector.

It is an advantage of the interface according to the present invention that a high degree of desired sample information relative to background solvent information can be attained, so that little or no loss of information occurs as a result of the solvent interference. For example, in EI mass spectrometry, sample molecular ions and fragments may be detected even though the masses may coincide with major ions produced from the solvent vapor.

Another advantage of the invention is that a substantial portion of the solvent vapor in the LC effluent is removed by the interface prior to entering a gas phase detector, such that the service life of pumps intended to maintain a desired system pressure level may be substantially prolonged.

It is another advantage of the present invention that the functional components of the interface of the present invention need not include moving parts, so that service and reliability of the interface is enhanced.

These and further objects, feature, and advantages of the present invention will become apparent from the following detailed description, wherein reference is made to the figures in the accompanying drawings.

DETAILED DESCRIPTION OF PREFERRED EMBODIMENTS

Figure 1:
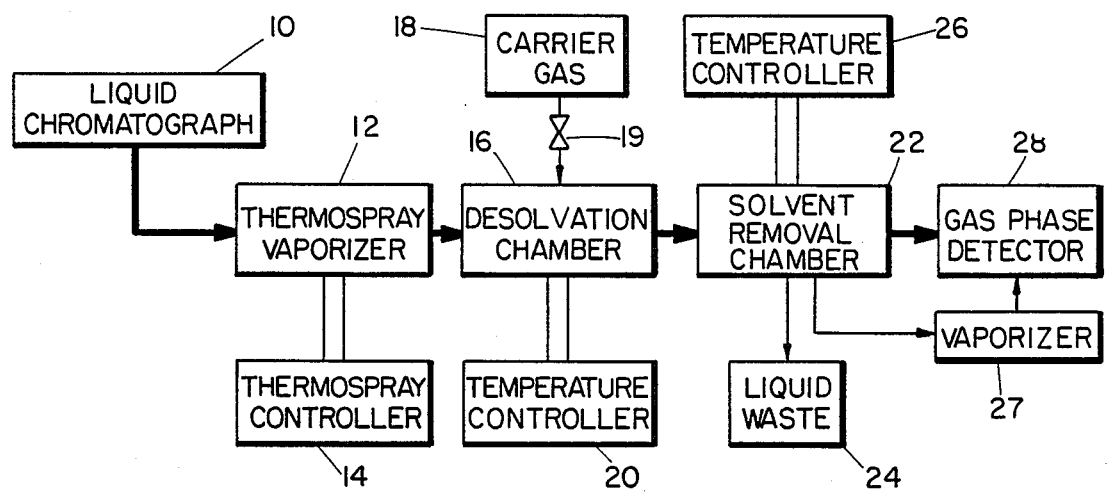
FIG. 1 is a block diagram illustrating the primary components of the liquid chromatographic device to gas phase detector interface according to the present invention.

The method and apparatus of the present invention are suitable for coupling LC effluent to various GC detectors. In some cases, it may be necessary to interpose means for vaporizing the sample particles immediately prior to the detector. For many gas phase detectors, it is not necessary to preserve the molecular integrity of the sample, and various conventional means may be used for vaporizing the particles even if thermal degradation of a sample occurs. Other detectors, such as mass spectrometry and FTIR, provide information regarding molecular weight and/or molecular structure, and accordingly it is essential to avoid pyrolysis or other uncontrolled chemical modification of the sample. Examples of gas phase detectors which may be used with the interface of the present invention are flame ionization detectors (FID), flame photometric detectors (FPD) for specific elements (such as P and S), thermionic ionization detectors (TID), atomic absorption (AA), photoionization, thermal conductivity, mass spectrometry, inductively coupled plasma detectors (ICP), and Fourier transform infra-red (FTIR).

In order to more fully appreciate the features and advantages of the present invention, a background discussion of vaporization and nebulization theory in a thermospray capillary is provided below.

Thermospray Vaporizer

When liquid is forced at high velocity through an unheated capillary tube, a solid jet issues from the tube, and breaks up into regular droplets according to Rayleigh's theory of liquid jet stabilty. Break up leads to droplets with uniform diameters approximately 2 times the diameter of the nozzle, and a train of droplets of a uniform size and velocity are thus produced. If the tube is heated gently, the properties of the jet are modified slightly by the drop in surface tension accompanying the increase in temperature, although little change is visually observed. When enough heat is applied to produce significant vaporization inside the capillary, the appearance of the jet changes drastically as it is partially vaporized and nebulized into a very large number of small droplets. A further increase in the applied heat reduces the visibility of the jet since the size of the droplets decreases due to further vaporization at high enough heat, and the only visual evidence of the jet is downstream condensation which occurs due to cooling.

A detailed analysis of the process occurring when liquid is vaporized as it is forced through a heated capillary tube is set forth in U.S. Pat. No. 4,730,111 and pending U.S. Application Serial No. 202,093 filed June 3, 1988, each hereby incorporated herein by reference. For purposes of the present discussion, it should be understood that the rate of vaporization, Z, of a liquid at temperature, T, is given by an equation
where $P_v(T)$ is the equilibrium vapor pressure at temperature T, Pa is the ambient pressure of the vapor, m is the molecular mass, and k is Boltzmann's constant. The effective vaporization velocity, $V_v$, may be obtained by multiplying the molecular mass and dividing by the density, $\rho_L$, of the liquid, such that The thermospray vaporizer shares many of the properties of a concentric pneumatic nebulizer used in atomic spectroscopy, in that a high velocity gas is used to shatter a liquid stream into a fine jet of droplets swept along in a gaseous stream. A significant feature of thermospray is that the nebulizing gas is generated in situ by partial vaporization of the liquid. Various attempts have been made to directly measure the droplet size distribution produced by thermospray, but these efforts have met with limited success primarily because a very large number of small, high velocity droplets are produced.

The total number of droplets produced per second $N_d$ may be determined by the volume of the unvaporized liquid divided by the average volume of the droplets at the instant of nebulization from the bulk liquid. This relationship may be expressed as
where F is the liquid flow rate expressed in mL/min., f is the fraction vaporized, and d is the droplet diameter in microns.

The rate of vaporization of a spherical liquid droplet, in turn, can be expressed by the equation
where r is the radius of the droplet, and $V_v$ is the net vaporization velocity calculated according to Equation 2. Since this rate is independent of r, the isothermal lifetime of a droplet can be expressed as a function of vaporization velocity. For water particles at 200° C. in the presence of water vapor at one atmosphere, the net velocity of vaporization is about 100 cm/sec. The isothermal lifetime of water droplets under these conditions is about 1 microsecond per micron radius. At 100° C., water droplets and its vapor at one atmosphere are in equilbrium, and the net rate of vaporization is zero. The very strong dependence of vaporization rates on temperature thus implies that the thermal environment of the droplet particles must be properly controlled for efficient vaporization and ion production.

It should be noted that the above analysis contains several unstated approximations and assumptions, which are probably not strictly valid. For example, it is assumed throughout that a single temperature characterizes the walls of the vaporizer, the vapor, and the liquid at any point along the vaporizer. Since heat is conducted from the walls of the vaporizer through the vapor to the liquid droplets, it is apparent that significant temperature differences must be involved.

If the initial droplet diameter and its thermal history were precisely known, then the droplet vaporization lifetime could be accurately calculated. In the absence of such detailed information, the parameters can be adjusted emperically to achieve complete vaporization of the solvent in the droplets at the exit from the desolvation chamber of the interface. The parameters which affect the droplet lifetime within the interface of the invention are accordingly the thermospray vaporization parameters, namely the temperature of the jetstream from the vaporizer, the diameter of the droplets, and the temperature and pressure of the carrier gas added to the desolvation chamber, which then determines the heat transfer to the droplets. If the sample is expected to contain components only slightly less volatile than the solvent, it may be necessary to carefully adjust thermospray conditions for the interface to achieve satisfactory transmission of volatile sample components while simultaneously efficiently removing the solvent.

LC to Detector Interfaces

Referring now to the drawings, FIG. 1 illustrates a block diagram of an interface according to the present invention. Effluent from a liquid chromatography (LC) unit 10 is directly coupled to a thermospray vaporizer 12, in which a controlled percentage of the solvent is vaporized while the remaining unvaporized solvent and sample particles are carried along as an aerosol in a high velocity vapor jet. The thermospray operation is carefully regulated by controller 14, which is described in detail in U.S. Pat. No. 4,730,111. The jet from the thermospray vaporizer 12 is introduced into a desolvation chamber 16, which may be heated sufficiently to further the vaporization process. Additional compressed and preferably inert gas, e.g. dry air, helium, or argon, is added from source 18 to the chamber 16 in sufficient quantity to maintain the desired pressure and flow rate. The flow rate of carrier gas may be carefully regulated by valve 19, as described below. The temperature of the desolvation chamber is closely regulated by temperature controller 20, so that all or essentially all of the solvent is vaporized within the chamber 16. The thermospray technique of the present invention allows very precise control of vaporization, so that the solvent can be vaporized while all or substantially all of the less volatile particles of interest will be retained. An aerosol consisting of vaporized sample particles, solvent vapor, and inert carrier gas will exit the desolvation chamber 16 and pass through one or more solvent removal chambers 22, where most of the solvent vapor is removed and discharged to liquid waste container 24. The resulting dry aerosol (unvaporized sample particles and inert carrier gas) is then transmitted to the gas phase detector 28, either directly or through one or more particle beam separators. The gas phase detector may be responsive to the sample particles of interest or to vapor from the sample particles of interest. In the latter case, a vaporizer 27 is provided between the condensers and the detector to achieve varporization of the particles of interest.

In one embodiment of the invention, the temperature of the desolvation chamber 16 is closely controlled by controller 20, while the temperature of the solvent removal chamber(s) 22 is controlled by temperature controller 26 so that solvent is removed by condensation, and the dry aerosol continues to the selected detector. The solvent vapor is thus carefully condensed by regulating controller 26 and the condensed solvent passed to waste container 24 while the less volatile materials continue on unaffected by the condensation process.

When thermospray is used to partially vaporize and nebulize the LC effluent, the desolvation 16 need not be controlled by a separate temperature controller 20, since the temperature of the spray in desolvation chamber 16 is sufficiently controlled by the vaporizer itself. For operation in this mode, it is preferable to operate the thermospray vaporizer close to, but below, the point of complete vaporization so that the vapor droplets exiting the vaporizer have sufficient heat content to provide the heat necessary to complete the vaporization during the expansion of the jet. Nevertheless, a separately heated desolvation chamber regulated by a controller 20 provides a convenient technique for completing the vaporization process started by the thermospray, and this temperature controlled desolvation chamber will often be required when using other types of nebulizers.

Referring now to FIG. 2, an embodiment of the interface is depicted in which the desolvation chamber employs a refrigerated condensor to remove the solvent vapor. In FIG. 2, the discharge end 30 of a thermospray vaporizer (which is fully described in U.S. Pat. No. 4,730,111) is installed in the desolvation chamber 34, such that a gas-tight connection is made between the vaporizer and the desolvation chamber. Controlled partial vaporization of solvent being discharged from end 30 is obtained by heater block 29 about the discharge end. The desolvation chamber 34 as shown in FIG. 2 is structurally a part of the solvent removal chamber, which in the depicted embodiment is a condenser, although it should be understood that a structurally separate desolvation chamber and condenser may be provided. The temperature within the chamber 34 is maintained by a sleeve-like heat block 36 in thermal contact with tube 40 to obtain the desired vaporization of the solvent in the LC effluent. A thermocouple 37 may thus be responsive to the temperature within chamber 34, to the temperature of the tube 40 in the heated zone of the desolvation chamber (as shown in FIG. 2), or to the temperature of the block 36. The output from thermocouple 37 is thus input to temperature controller 20, which regulates the heating of 36 to obtain the desired vaporization. The zone of the interface heated by block 36 should be sufficiently long to allow the particles to approch their thermal equilibrium with the vapor phase. The minimum temperature for complete vaporization of the solvent is then the temperature at which the vapor pressure of the solvent is just greater than the partial pressure of the completely vaporized solvent at the particular flow rate of the liquid employed. Ideally, effluent from the desolvation chamber 34 consists of nearly dry particles of unvaporized sample, solvent vapor at a partial pressure somewhat less than one half of the total pressure, and carrier gas.

An appropriate carrier gas is introduced into the desolvation chamber 34 through port 38, and preferably flows in the annulus between the chamber interior sidewalls 35 and the vaporizer probe 30 to entrain the droplets produced in the thermospray jet. At the discharge end of the thermospray probe 30, the carrier gas is thus moving axially with and surrounds the thermospray jet. In general, the flow rate of the carrier gas should be at least equal to the vapor flow produced by the complete vaporization of the liquid input to the vaporizer. If the LC sample contains volatile components, however, it may be desirable to use a higher gas flow rate so that the liquid can be vaporized at a lower temperature.

Figure 3:
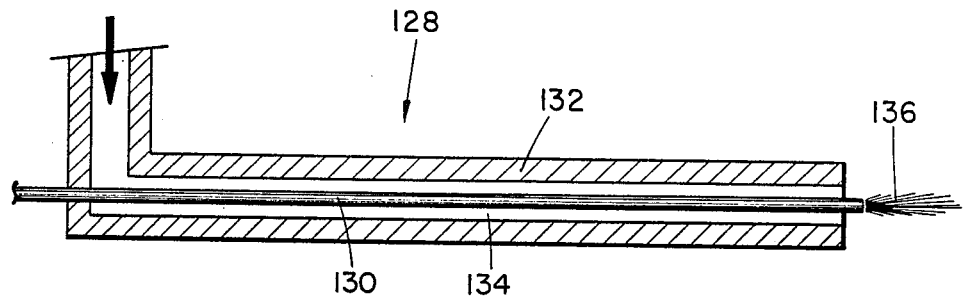
FIG. 3 is simplified pictural illustration of an alternative version of a thermospray vaporizer which provides a concentric flow of heated carrier gas.

Instead of a standard thermospray vaporizer as described above, a modified thermospray vaporizer 128 such as that depicted in FIG. 3 may be employed. In this configuration, the liquid from the chromatograph is carried through an inner capillary tube 130 which may be conveniently made from fused silica or from stainless steel hypodermic needle tubing. An outer tube 132 of stainless steel is heated directly by passing a current through it, and the heat input is controlled as described in detail in U.S. Pat. No. 4,730,111. The carrier gas is transmitted through the annular space 134 between the inner and outer tube. With this device, both the LC effluent and the carrier gas are heated and the high velocity of heated carrier gas discharged surrounding the thermospray jet 136 assists in dispersing and vaporizing the droplets in the jet.

Figure 2:
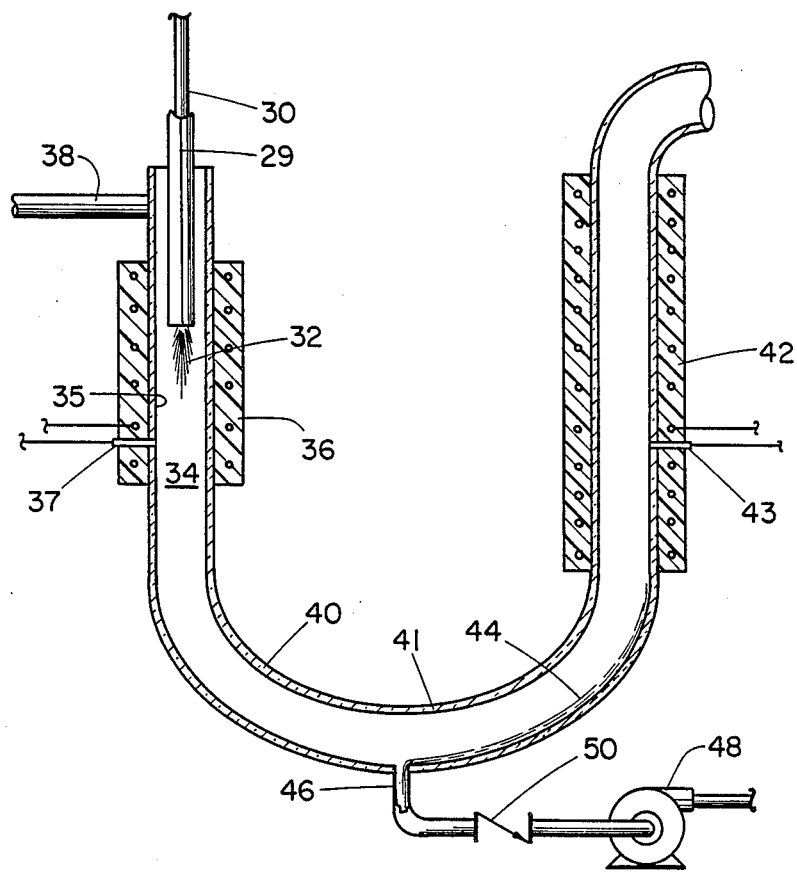
FIG. 2 is a simplified pictorial view of one embodiment of an interface according to the present invention.

Although flow velocities through the interface are not critical, carrier gas flow must be sufficiently high to effectively transport the aerosol while causing minimal turbulence. A tube 40 with a circular interior cross-section of a diameter approximating one centimeter is satisfactory for flow rates obtained with LC liquid inputs up to at least 2 mL/minute. A uniform cross-section of the flow path throughout the desolvation chamber and condensers is preferred, and sudden changes in the cross-section which would result in rapid expansion or contraction of the flow rate should be avoided. Although the aerosol may be passed through an arcuate path, as shown in FIG. 2, sharp bends in the flow path should be avoided so that particles do not impact the interior sidewalls of the tube 40 and accordingly may pass to the selected detector. Under preferred flow conditions, essentially laminar flow is maintained in tube 40, and the aerosol is carried by the higher velocity carrier gas through the center of the tube, thereby allowing the particles to be transported along comparatively long distances with negligible losses. In view of the large mass of these particles relative to that of the carrier gas and solvent gas molecules, diffusion of the aerosol particles to the walls is small, while diffusion of solvent molecules in the carrier gas is relatively rapid.

As effluent passes through tube 40 from the heated zone of the desolvation chamber to the cooler zone of the condenser, it becomes supersaturated and begins to condense on the walls of the tube 40. Condensation of vapor on the sample particles will be minimal since the sample particles near the center of the tube 40 will normally be somewhat warmer than the vapor in contact with the cooler walls, and since the total surface area of the particles will normally be considerably smaller than the surface area of the cool tube. The temperature of the sleeve-like cooling jacket 42 in thermal contact with the tube 40 may be adjusted so that the inner wall temperature is only slightly above the freezing point of the condensed liquid. A thermocouple 43 is provided for sensing and transmitting to controller 26 a signal indicative of the inner wall temperature in the condenser, and controller 26 regulates jacket 42 in response thereto.

The tube 40 is thus provided with a transition region or section 41 between the heated zone of the desolvation chamber and the cooled zone of the condenser. The transition region 41 is arranged, as shown in FIG. 2, so that the liquid condensate 44 preferably flows under the affects of gravity to the drain 46 in the transition region 41 of tube 40, where the condensate is pumped away to waste. A small positive displacement pump 48, such as a peristaltic tubing pump, may be used to pump away the condensate without allowing a significant amount of gas or vapor to escape from the interface. The drain may be equipped with a conventional check valve 50 to prevent backflow of liquid in the event that the interior pressure of the interface should drop below the outside pressure.

Assuming a sufficient length of cool zone is provided in the condenser, the vapor exiting the condenser approaches equilibrium with the liquid at the temperature of the condenser. A condenser employing a straight tube approximately 30 centimeters in length has been found to be satisfactory for LC liquid input flow rates up to 0.5 Ml/minute. The length of the flow path from the desolvation chamber to the condensers should be at least 30 times, and preferably at least 50 times, the diameter or width of the flow path. For applications at higher liquid flow rates, the total length of the cool zone should be increased in proportion to the maximum liquid flow anticipated. The condenser can be configured to cool the tube 40 arranged in a helical form, thereby effectively increasing the cooled length of the tube 40 without increasing the size of the condenser. A helical pattern for the tube 40 would also introduce some angular momentum into the flow, which can increase the effective diffusion coefficient and correspondingly increase the efficiency of the condenser.

A relatively simple interface as depicted in FIG. 2 may provide efficient solvent removal for some LC to gas phase detector applications. For example, if the detector is an electron impact mass spectrometer equipped with a two-stage particle beam separator which further reduces solvent vapor transmission, the combination of the interface and the particular detector may result in efficient solvent removal efficiency while transmitting more than one half of the sample particles. The embodiment shown in FIG. 2 may thus result in good detector sensitivity for many samples, even though there is still significant contribution to the low mass portion of the mass spectrum by ionization of solvent vapor. With the condenser as depicted in FIG. 2 cooled to 0° C., more than 99% of the water can be condensed and removed, while more than 90% of typical organic solvents, such as methanol or acetonitrile, may be removed. The condensor of the present invention is able to remove substantially all, and preferably at least 90% of the solvent in the LC effluent which is discharged into the desolvation chamber. Solvent removal efficiency of more than 95% can be obtained by programming the temperature of the condenser according to the composition of the LC mobile phase. The temperature of the condenser should, however, not be less than the freezing point of the liquid mixture input, or solid waste build up in the condenser may clog the interface. Since it is often desirable to detect samples separated by liquid chromatography at concentrations at the part per billion level or even lower, a further reduction in solvent concentration beyond that obtainable with the interface as shown in FIG. 2 may be required for many applications.

Figure 4:
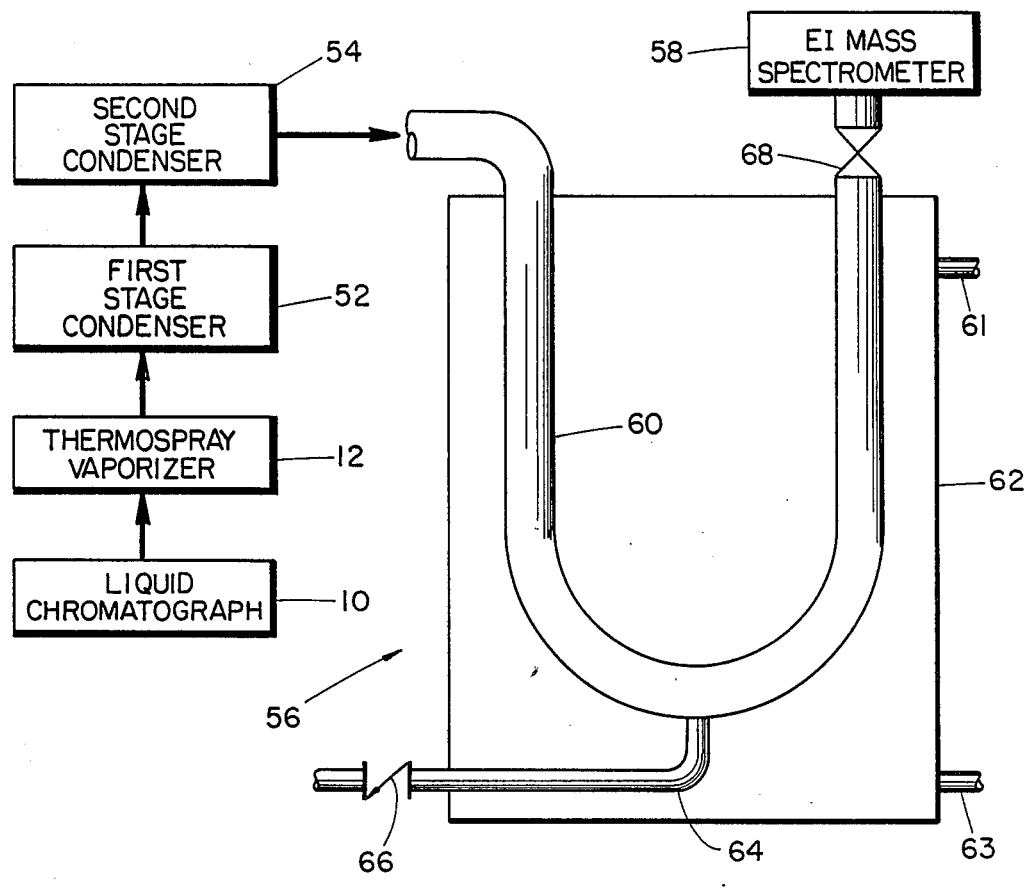
FIG. 4 is a partial block diagram and partial pictorial view of another embodiment of an interface according to the present invention.

FIG. 4 depicts a system which will enable a further reduction in solvent vapor concentration compared to the interface as shown in FIG. 2. The interface as shown in FIG. 4 includes a first stage condenser 52, which may be structurally and functionally identical to that depicted in FIG. 2. A second stage condenser 54 is added in series to first stage condenser 52, with the second stage unit 54 being structurally similar to that shown in FIG. 2, but with no additional carrier gas or thermospray jet provided, and thus no heated zone or block 36. Accordingly, the second stage condenser 46 comprises a U-tube in series with the U-tube of the first stage condenser, a second stage drain, and a second stage cooled zone or jacket 42 downstream from the drain. An cyrogenic trap 56 as shown in FIG. 4 is then added in series after the second stage condenser 54, with its effluent passing to a suitable gas phase detector, such as an EI mass spectrometer 58.

For the interface depicted in FIG. 4, the first stage condenser 52 is preferably operated at a temperature just above the freezing point of the input solvent composition, while the second stage condenser 54 is preferably operated at a temperature just above the freezing point of the remaining solvent vapor composition transmitted by the first condenser, so that the second stage condenses without freezing the maximum amount of solvent vapor. Between the first and second condenser stages, the vapor and aerosol pass through a section of tube 0 maintained at ambient temperature. This allows any solvent which may have condensed on the particles in the first stage condensers 54 to be revaporized, and subsequently condensed off the particles in the second stage condenser 56 with most of the remaining vapor. If the second stage condenser is operated at approximately $-40°$ C., then more than 99% of organic solvents will be removed by the first and second stage condensers, along with all or almost all of the water. If a further reduction of solvent vapor concentration is required, the effluent from the second stage condenser 54 may be transported through tube 60 which is positioned within a sealed housing 62 immersed in a suitable coolant, such as a liquid nitrogen. The housing 62 may thus contain a liquid nitrogen inlet 61 and an outlet 63 which maintain the tube 60 at a sufficiently low temperature to effectively remove most of the remaining solvent vapor. This cyrogenic trap 56 thus will cause almost all of the remaining solvent to be trapped in solid form on the inner surface of the tube. Unlike the first and second stage condensers in which the condensate is continuously withdrawn in liquid form, cyrogenic trap 56 cannot be operated continuously. However, since only a small amount of condensable material is transmitted to the trap 56 from the second stage condenser 54, it can be operated for extended period (more than 8 hours) until sufficient solid buildup on the inside of tube 60 has occurred to require its removal. Removal of the buildup may be accomplished by closing the valve 68 connecting the output of the trap 68 to the detector, and removing the nitrogen coolant. By allowing the trap to warm to room temperature and then opening the drain valve 64, the accumulated condensate will be blow out past check valve 66 to waste.

The performance of the interface according to the present invention depends to some extent on the size of the particles produced. Smaller particles are easily accelerated in the spray nozzle, and are also more easily deflected by flowing gas streams downstream of a nozzle. On the other hand, larger particles are more difficult to accelerate and require higher carrier gas velocities to maintain them as an aerosol, but once accelerated are not easily deflected from the particle beam. In the absence of nonvolatile material other than the sample of interest in the liquid stream, the final diameter of the dry particle will depend on the sample concentration in the unvaporized liquid. This feature may have the undesirable effect that the sample transfer efficiency may depend on the final particle size and hence the concentration of the sample in the unvaporized liquid, so that there is non-linearity in the detector response, particularly at low sample concentrations. This undesirable effect may be avoided by adding to the mobile phase a low concentration of a material, e.g., urea, having lower volatility than the solvent, so that its concentration rather than that of the sample determines the final particle size. If this added material is selected so that the detector does not respond significantly due to its presence, then the desired linear detector response to samples of interest can be achieved, and high detector sensitivity maintained. Also, the selected material may be chosen to enhance gas phase detection of selected types of compounds, while surpressing detection of compounds of little or no interest.

Figure 5:
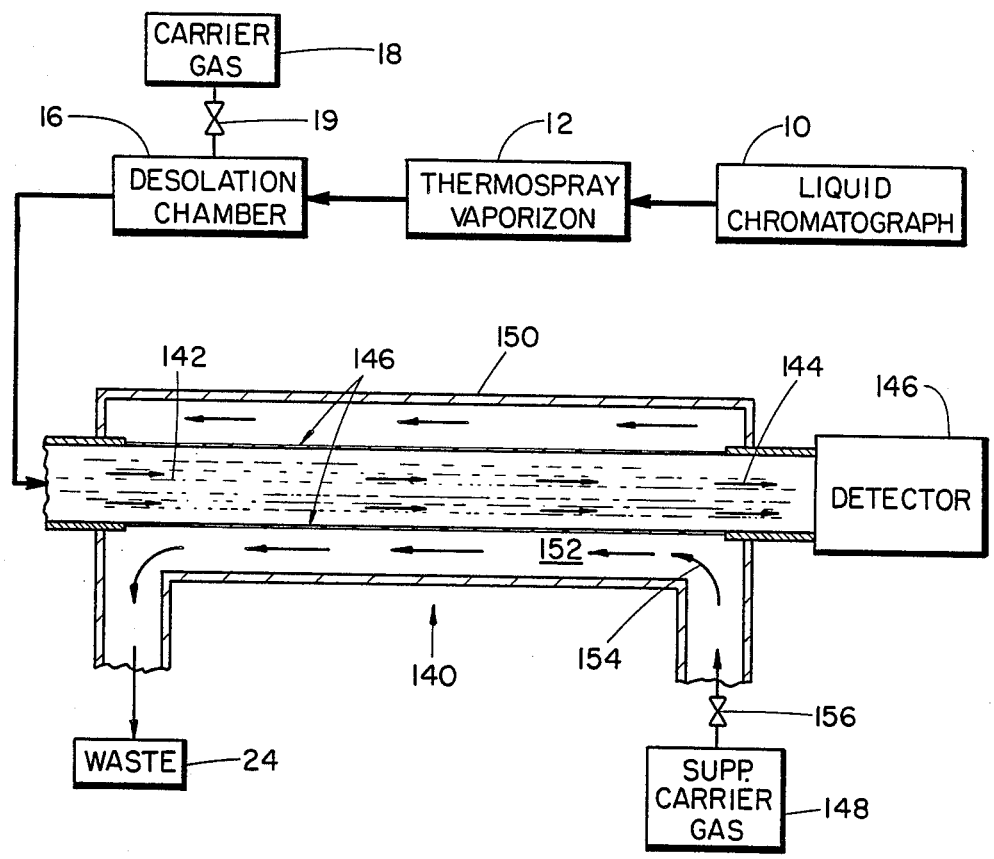
FIG. 5 is a partial block diagram and partial pictorial view of another embodiment of an interface according to the present invention.

An alternative method for accomplishing solvent vapor removal is depicted in FIG. 5. In this embodiment, the refrigerated condensors are replaced by a gas diffusion cell 140. A "wet aerosol" mixture 142 consisting of carrier gas, solvent vapor, and sample particles from the desolvation chamber 16 enters the diffusion cell 140, and a "dry aerosol" mixture 144 consisting substantially of carrier gas and sample particles of interest passes to the detector 146. The sample particles passing through the diffusion cell are separated from a supplemental carrier gas flow by a diffusion membrane 146. Gas, preferably chemically identical to the carrier gas introduced to the desolvation chamber, is input from container 148 into the diffusion cell housing 150, and flows in the annulus 152 between the housing 150 and membrane 146 in a counterflow direction to the flow of particles through the diffusion cell. In this device, the flow rate of the counterflowing supplemental gas must be significantly greater than the flow rate of the wet aerosol mixture, and is preferably two or more times greater, so that at each point along the membrane 146 the concentration of solvent vapor in the counterflow gas is significantly lower than that in the wet aerosol. The flow rate of supplemental carrier gas 154 may be closely controlled by valve 156. The properties of the membrane 146 are not critical, and a variety of filter media have been used successfully. The membrane should be sufficiently permeable that the carrier gas and vapor can diffuse freely across it, yet be a sufficient barrier to flow that any net flow of gas through the membrane is relatively small, and so that no particles of interest pass therethrough. A membrane formed from a fibrous porous form of PTFE has been found to be satisfactory, and such a suitable material is commercially available under the tradename "ZITEX."

The above approach has the advantage over the refrigerated condensors since no expensive mechanical components, such as refrigerators and pumps, are required, but has a minor disadvantage in that a higher total flow of carrier gas is required. The effective area of the diffusion cell, i.e., the area of membrane 146 separating the particles in the primary flow from the supplemental carrier gas 154, may be easily controlled to remove the desired amount of solvent vapor. Also, the gas diffusion cell 140 may be used in series with the refrigerated condensors. For example, the diffusion cell 140 may replace the cryogenic trap discussed previously and shown in FIG. 4, so that a combination of first and second stage refrigerated condensors 52 and 54 followed by a diffusion cell 140 provides the desired solvent removal.

Once the sample has reached the specific detector desired, it may be treated as required by the properties of the particular detection device employed in order to attain maximum detection efficiency for the sample. With gas phase detectors such as PID or FID, the sample particles can be extensively heated in the gas stream and caused to impact on a heated surface, since pyrolysis is not detrimental and only a portion of sample need be converted to gas so that it may be detected. In other cases, additional conventional elements may be required to complete the coupling between the interface and the paticular detector. Those skilled in the art should thus appreciate that the interface of the present invention can be combined with almost any of the wide range of gas phase and solid phase detectors, so that an essentially "universal" detector between liquid chromatography and gas phase detectors is obtained.

Detector Applications

Figure 6:
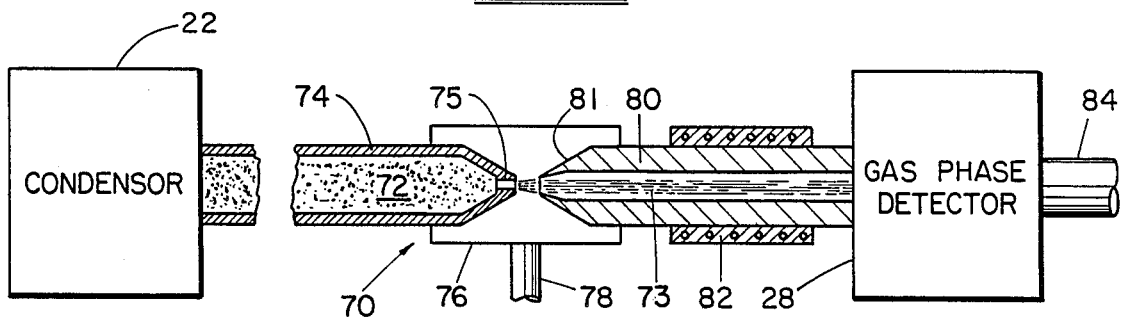
FIG. 6 is a simplified pictorial illustration of a portion of an interface according to the present invention connected to a suitable gas phase detector.

The interface of the present invention may be effectively used for coupling LC effluent to a wide variety of detectors. Referring now to FIG. 6, a portion of an interface 70 is shown which, in accordance with the foregoing description, converts aerosol samples 72 less volatile than the LC solvent into a particle beam 73 which is efficiently transmitted to a gas phase detector 28. Solvent vapor is efficiently removed and replaced with a carrier gas at essentionally atmospheric pressure, the added gas being suitable as a carrier gas for use with the particular selected detector. According to one embodiment, the aerosol from one or more condensers 22 may be directly input at atmospheric pressure through flow tube 74 to a selected gas phase detector 28, which is vented to atmosphere.

For other gas phase detectors, it may be necessary to reduce the flow rate to the detector and provide a heating means to vaporize the particles to provide a sample vapor which can be detected. FIG. 6 illustrates a flow tube 74 from one or a series of condensers 22, wherein the aerosol flow (rate of from 0.5 to 2.0 L/minute) is substantially restricted at nozzle 75, which discharges a particle beam through momentum separator 76 and into tube 80. Gas or vapor may thus be vented from separator 76 through vent line 78, so that the beam 73 in tube 80 is at substantially atmospheric pressure. The flow rate in the tube 80 may be restricted, for example, by entrance skimmer 81, so that the detector 28 may be vented to atmosphere at 84, with vent 84 discharging a small fraction, e.g. from 10 to 100 mL/min., of the flow rate from the condensers 22. The tube 80 depicted in FIG. 6 is shown with a sleeve-like heating unit 82 in thermal contact with tube 80 to vaporize the sample particles passing through the tube 80, and thus transmit a sample vapor to the detector 28. For still other gas phase detectors, it may be possible to accomplish vaporization of the sample particles directly as the sample is ionized and detected, e.g. in a flame.

Figure 7:
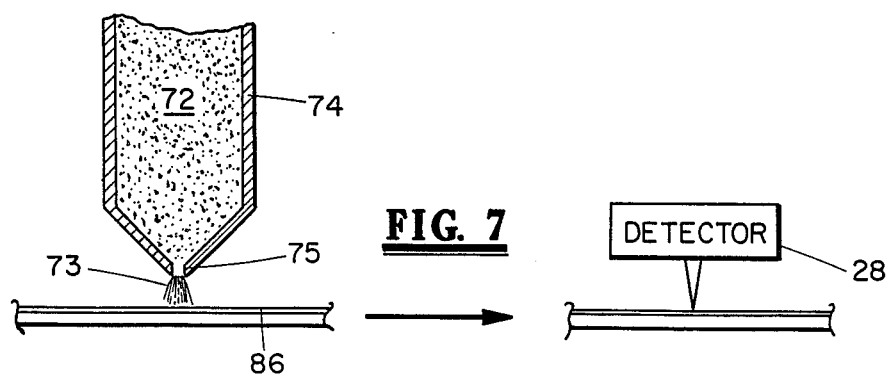
FIG. 7 is a pictorial view of a portion of an interface according to the present invention for depositing the sample on a solid surface for subsequent analysis by a solid phase or gas phase detector.

FIG. 7 depicts a portion of a thermospray interface according to the present invention coupled to a detector 28 which is responsive to sample deposited on a solid surface. Accordingly, the flow tube 74 from the condensers is restricted by nozzle 75 to discharge a particle beam 73 which impinges a moving or movable surface 86, such as a ribbon, plate, or drum. The sample separated by liquid chromatography are thus deposited at different locations on the moving surface 86, and can subsequently be analyzed or detected by an appropriate surface sensitive technique, such as diffuse reflectance FTIR, secondary ion mass spectrometry (SIMS) or Cf-252 plasma desorption mass spectrometry. In each of these cases, a solid may be added in solution to the mobile phase upstream of the vaporizer, which can then serve as a solid carrier to enhance the transmission of samples of low concentration to the detector 28, and also enhance detection of the samples of interest. For example, potassium chloride could be added to provide a transparent matrix for FTIR detection. Alternatively, organic solids such as nitrocellulose or tartaric acid, may be added upstream of the vaporizor to enhance the performance of a mass spectrometry detector.

Figure 8:
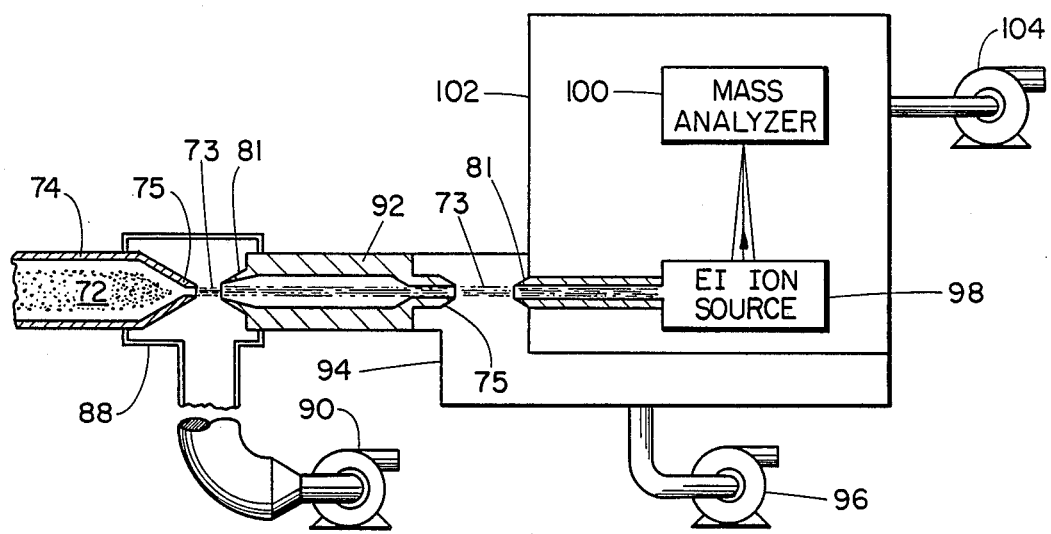
FIG. 8 illustrates a portion of an interface according to the present invention for coupling LC to electron impact mass spectrometry analysis.

FIG. 8 illustrates a thermospray interface according to the present invention used to couple liquid chromatography to electron impact mass spectrometry. Since EI mass spectrometry requires a relatively good vacuum in the ion source and mass analyzer, additional pumping capability is provided to reduce the pressure of the carrier gas before it reaches the ion source, while simultaneously efficiently transmitting the particle beam. As illustrated in FIG. 8, tandem momentum separators are employed, and the selected carrier gas is preferably a low molecular weight inert gas, such as helium. The discharge from flow tube 74 passes through a first momentum separator 88, which is evacuated to a pressure of a few torr by a suitable mechanical vacuum pump 96 with the capacity of approximately 4 liters per second. The particle beam continues to pass through tube 92, with the flow rate further reduced by skimmer 81 as previously described, and is discharged into a second momentum separator 94 evacuated to a pressure of about 0.001 torr or less by a diffusion pump 96 with a capacity of about 400 liters per second. By properly choosing the nozzle and skimmer orifices, and by regulating the distance between the nozzle 75 and the skimmer 81 in either or both of the first and second momentum separators 88 and 94, the remaining particle beam may be effectively transmitted to the EI ion source 98 and the mass spectrometer 100, while most of the carrier gas is pumped away by 90 and 96. A small fraction of the carrier gas may, of course, reach the ion source 98, but a low mass and small ionization cross-section carrier gas (e.g. helium) in small concentration will not seriously degrade the performance of the EI mass spectrometer, e.g. when its pressure is less than about 0.0001 torr. As shown in FIG. 8, the EI ion source 98 and mass analyzer 100 may be conveniently housed within chamber 102, in which vacuum is effectively controlled to the extent desired for EI mass spectrometry by pump 104.

Figure 9:
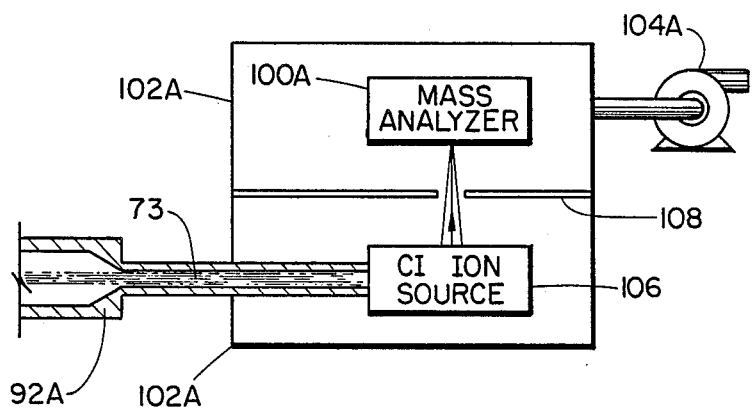
FIG. 9 illustrates a portion of the interface according to the present invention for coupling LC to chemical ionization mass spectrometry analysis.

FIG. 9 depicts a thermospray interface for coupling liquid chromatography to chemical ionization mass spectrometry. This technique is similar to that employed for EI mass spectrometry, but only a single momentum separator is required, since the CI ion source 106 operates at a much higher pressure of, for example, 1 torr. The aerosol thus passes through a single momentum separator 88 as shown in FIG. 8, with the particle beam 73 continuing through tube 92A similar to that shown in FIG. 8. In this case, however, the particle beam is directly input to CI ion source 106, and the ions passed through baffles 108 and analyzed by mass analyzer 100A. The CI ion source 106 and analyzer 100A are appropriately housed in chamber 102A, with the necessary vacuum for CI mass spectrometry regulated by pump 104A. In this case, a desired chemical ionization reagent gas may be introduced with the carrier gas to the interface, or helium can be used as the carrier gas and the reagent introduced directly into the ion source 106 at a very low flow rate.

Figure 10:
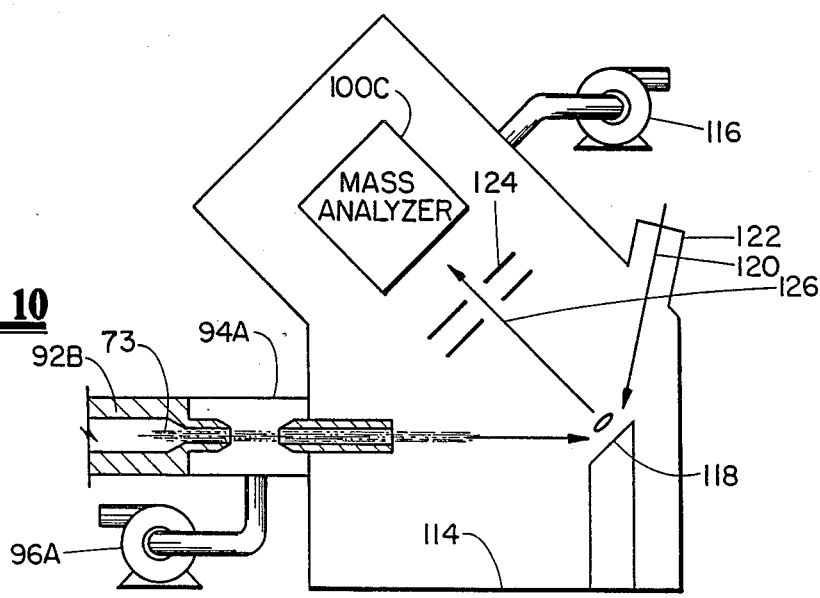
FIG. 10 is a pictorial view of a portion of an interface according to the present invention for coupling LC to a temperature controlled surface for laser desorption analysis.

FIG. 9 depicts a thermospray interface for transmitting a sample particle beam to a surface in an evacuated detection instrument. The detector in the particular configuration depicted is for laser desorption mass spectrometry, although secondary ion mass spectrometry, matrix isolation FTIR, or other detector requiring a high vacuum may be used. For FTIR, argon may be used as the carrier gas so that a small fraction of the transmitted gas impacts a cyrogenically cooled surface upon which both the sample and the gas are condensed and subsequently analyzed. The impacted surface may be either heated or cooled, and the sample contained in the particle beam 73 may be collected on the surface and simultaneously vaporized, or ionized by either focused laser radiation or by impact from high energy ions or neutrals. Alternatively, the samples may be vaporized by heating the surface, either directly or by irradiation from a laser or ion beam, and the samples then vaporized and ionized by electronic impact using auxillary electron beam techniques. FIG. 10 thus depicts a flow tube 92B similar to that previously described for receiving aerosol passed through a single momentum separator 88, and transmitting the particle beam 73 to a second momentum separator 94A with its vacuum maintained by vacuum pump 96A. The particle beam continues on to impact temperature controlled surface 118, where the sample is vaporized and ionized by laser beam 120 input to chamber 114 through port 122. The sample ions 126 pass through baffles 124, and thence to mass analyzer 100C. Appropriate vacuum for the analysis is maintained by pump 116.

It should be understood that various nebulizers may be used for discharging an LC effluent spray into a desolvation chamber according to the present invention, although thermospray techniques which include the controlled partial vaporization of the effluent prior to discharge are preferred. Also, if a nebulizer technique other than thermospray is used, it would be preferred to heat the LC effluent prior to spraying into the desolvation chamber, so that complete vaporization of the solvent in the desolvation chamber can reliably occur at reasonable LC flow rates without significant vaporization of the sample particles of interest. The techniques of the present invention are applicable, however, to various nebulizers for discharging LC effluent into the desolvation chamber, such as variations of the MAGIC or thermabeam concepts discussed earlier.

It should also be understood that a particular solvent may be selected for carrying the samples of interest (solute) through the chromatographic device which will be dependent upon the selected chromatographic unit and the samples to be separated by the process. Preferably, there is a significant disparity between the volatility of the solvent and the volatility of the samples of interest, such that complete vaporization of the solvent occurs within the interface of the present invention without there being a significant vaporization of the samples of interest.

It should be understood that various types of gas phase and solid phase detectors may be used with the substantially universal interface of the present invention for coupling LC effluent to a desired detector. Although some modifications of the equipment downstream from the desolvation chamber and condensers may be beneficial or necessary, the same basic interface may be used with various gas phase detectors, thereby enhancing versatility of the interface and reducing manufacturing costs.

The foregoing disclosure and description of the invention is illustrative and explanatory thereof, and various changes in the size, shape and materials as well as in the details of the illustrated construction may be made within the scope of the appended claims without departing from the spirit of the invention.

What is claimed is:

1. An improved interface for receiving liquid effluent including sample solute of interest and solvent from a liquid chromatographic device and outputting sample particles of interest to a detector for analysis of a sample, the interface comprising:

a desolvation chamber;

desolvation chamber heating means for heating the sprayed effluent within the desolvation chamber to vaporize substantially all solvent within the desolvation chamber while maintaining the sample particles of interest in the desolvation chamber;

spraying means for discharging the heated liquid effluent into the desolvation chamber;

gas supply means for inputting a carrier gas to the desolvation chamber;

flow path means for transferring an aerosol including the carrier gas, vaporized solvent, and the sample particles of interest from the desolvation chamber; and solvent removal means for receiving the aerosol and removing substantially all of the vaporized solvent while outputting the carrier gas and substantially all of the sample particles of interest to the detector for analysis, the solvent removal means including a cell housing, a gas diffusion membrane within the cell housing and separating the cell housing into a primary flow chamber for receiving the aerosol and an adjoining secondary flow chamber and supplemental carrier gas supply means for passing carrier gas through the secondary flow chamber while aerosol is passed through the primary flow chamber such that solvent vapor is diffused through the membrane from the primary flow chamber to the secondary flow chamber and is removed by the supplemental carrier gas.

2. A improved interface as defined in claim 1, further comprising:

thermospray controller means for regulating thermal output of the heating means to vaporize a substantial portion of the solvent from the liquid chromatographic device prior to being discharged into the desolvation chamber.

3. An improved interface as defined in claim 1, wherein the solvent removal means further comprises:
condensor means for cooling the aerosol and condensing substantially all the vaporized solvent therein into liquid solvent.

4. An improved interface as defined in claim 3, further comprising:
a liquid waste drain in fluid communication with the flow path means for continuously outputting the condensed liquid solvent from the condenser means while the aerosol is transferred through the flow path means to the condenser means; and
the flow path means being configured such that substantially all condensed liquid vapor within the condenser means flows through a portion of the flow path means to the liquid waste drain in a counterflow direction to aerosol flow through the portion of the flow path means.

5. An improved interface as defined in claim 3, wherein the condenser means further comprises:
first and second cooling means serially spaced for cooling the aerosol at respective first and second serially spaced locations within the condenser means; and
a transition section between the first and second cooling means for revaporizing condensed solvent carried on the particles of interest passing by the first cooling means and recondensing the solvent off the particles of interest with the second cooling means.

6. An improved interface as defined in claim 3, further comprising:
condenser temperature control means for controlling the temperature of the aerosol passing through the condenser means for removing in excess of 99% of the solvent vapor within the aerosol passing through the flow path means such that a low concentration of solvent vapor is output to the detector.

7. An improved interface as defined in claim 1, wherein cross-sectional flow area of the flow path means remains substantially uniform such that rapid expansion or contraction of the aerosol is minimized or prevented.

8. An improved interface as defined in claim 7, wherein the desolvation chamber, the flow path means, and the solvent removal means are each configured such that abrupt directional changes of flowing aerosol are avoided.

9. An improved interface as defined in claim 4, further comprising:
a substantially uniform diameter flow tube defining the cross-sectional flow area within the desolvation chamber, the flow path means, and the solvent removal means.

10. An improved interface as defined in claim 1, wherein the flow path means has a length at least thirty times the cross-sectional diameter of the flow path means.

11. An improved interface as defined in claim 1, further comprising:
carrier gas control means for regulating carrier gas flow rate into the desolvation chamber such that the carrier gas flow rate is greater than the flow rate of vapor discharged into the desolvation chamber from the spraying means.

12. An improved interface as defined in claim 1, wherein:
a discharge end of the spraying means is positioned within the desolvation chamber; and
the gas supply means inputs carrier gas within the desolvation chamber circumferentially about the discharge end of the spraying means such that the carrier gas flows within the desolvation chamber axially toward the discharge end of the spraying means to prevent the aerosol from contacting sidewalls of the flow path means.

13. An improved interface as defined in claim 1, further comprising:
vapor temperature sensing means for sensing the temperature of the solvent vapor within the desolvation chamber and generating a signal to the desolvation chamber heating means in response thereto.

14. An improved interface as defined in claim 1, further comprising:
temperature control means for regulating the desolvation chamber heating means; and
the desolvation chamber heating means increases the temperature of the particles of interest within the desolvation chamber to a temperature approaching thermal equilibrium with the vaporized solvent within the desolvation chamber.

15. An improved interface as defined in claim 3, further comprising:
vapor temperature sensing means for sensing the temperature of the solvent vapor in the condensing means and generating a signal to the condensing means in response thereto.

16. An improved interface as defined in claim 3, wherein the condensing means comprises:
cooling means for continually condensing at least a substantial portion of the solvent vapor received by the condensing means;
a liquid drain for removing the condensed solvent from the cooling means; and
a cyrogenic trap downstream from the cooling means for collecting in solid form remaining solvent vapor which passes by the cooling means, such that substantially only carrier gas and particles of interest are passed to the detector.

17. An improved interface as defined in claim 16, further comprising:
condenser temperature control means for regulating the cooling means to maintain condensed solvent within the condenser means at a temperature above the freezing point of the condensed solvent.

18. An improved interface as defined in claim 1, further comprising:
the detector is a gas phase detector; and
vaporizing means for vaporizing the particles of interest output from the solvent removal means to produce vapor for analysis by the gas phase detector.

19. An improved interface as defined in claim 1, further comprising:
a moving surface means; and
the particles of interest from the solvent removal means are deposited on the moving surface means for analysis by the detector.

20. An improved interface as defined in claim 1, further comprising:
first and second momentum separators for removing carrier gas from the particles of interest; and means for connecting the interface to the detector, wherein the detector is an electron impact mass spectrometer.

21. An improved interface as defined in claim 20, wherein:
each of the first and second momentum separators includes a nozzle and an axially spaced skimmer for controlling the amount of carrier gas passed with the particles of interest to the detector.

22. An improved interface as defined in claim 1, further comprising:
reagent gas supply means for adding reagent gas to the carrier gas input to the desolvation chamber; and means for connecting the interface to the detector, wherein the detector is a chemical ionization mass spectrometer.

23. An improved interface for receiving liquid effluent including sample solute and solvent from a liquid chromatograhic device and outputting sample particles of interest to a detector for analysis of a sample, the interface comprising;
a desolvation chamber;
spraying means for discharging the liquid effluent into the desolvation chamber;
heating means for heating the sprayed effluent within the desolvation chamber to vaporize substantially all solvent within the desolvation chamber while maintaining the sample particles of interest in the desolvation chamber;
gas supply means for inputting a carrier gas to the desolvation chamber;
solvent removal means for receiving the transmitted aerosol and removing most of the vaporized solvent while outputting the carrier gas and substantially all of the sample particles of interest to the detector for analysis the solvent removal means including a gas diffusion cell means for diffusing solvent from the aerosol while outputting carrier gas and sample particles of interest to the detector, the gas diffusion cell means having a cell housing, a gas diffusion membrane within the cell housing and separating the cell housing in a primary flow chamber for receiving the aerosol and an adjoining secondary flow chamber and supplemental carrier gas supply means for passing carrier gas through the secondary flow chamber while aerosol is passed through the primary flow chamber such that solvent vapor is diffused through the membrane from the primary flow chamber to the secondary flow chamber and is removed by the supplemental carrier gas; and
a waste drain for continuously outputting solvent from the solvent removal means while the aerosol is transferred through the flow path means.

24. An improved interface as defined in claim 23, further comprising:
liquid effluent heating means for heating the liquid effluent prior to entering the desolvation chamber; and
thermospray controller means for regulating thermal output of the liquid effluent heating means to vaporize a substantial portion of the solvent from the liquid chromatographic device prior to being discharged into the desolvation chamber.

25. An improved interface as defined in claim 23, wherein the solvent removal means comprises:
condensor means for cooling the aerosol and condensing substantially all the vaporized solvent therein into liquid solvent.

26. An improved surface as defined in claim 25, wherein the condenser means further comprises:
first and second cooling means serially spaced for cooling the aerosol at respective first and second serially spaced locations within the condenser means; and
a transition section between the first and second cooling means for revaporizing condensed solvent carried on the particles of interest passing by the first cooling means and recondensing the solvent off the particles of interest with the second cooling means.

27. An improved interface as defined in claim 23, further comprising:
carrier gas control means for regulating carrier gas flow rate into the desolvation chamber such that the carrier gas flow rate is greater than the flow rate of vapor discharged into the desolvation chamber from the spraying means.

28. An improved interface as defined in claim 23, wherein:
a discharge end of the spraying means is positioned within the desolvation chamber; and
the gas supply means inputs the carrier gas within the desolvation chamber circumferentially about the discharge end of the spraying means such that the carrier gas flows within the desolvation chamber axially toward the discharge end of the spraying means to prevent the aerosol from contacting sidewalls of the flow path means.

29. An improved interface as defined in claim 25, further comprising:
first vapor temperature sensing means for sensing the temperature of the solvent vapor within the desolvation chamber and generating a signal to the heating means in response thereto; and
second vapor temperature sensing means for sensing the temperature of the solvent vapor in the condensing means and generating a signal to the condensing means in response thereto.

30. An improved interface as defined in claim 25, wherein the condensing means comprises:
cooling means for continually condensing at least a substantial portion of the solvent vapor received by the condensing means and passing the condensed solvent to the waste drain; and
a cyrogenic trap downstream from the cooling means for collecting in solid form remaining solvent vapor which passes by the cooling means, such that substantially only carrier gas and particles of interest are passed to the detector.

31. An improved interface as defined in claim 23, further comprising:
vaporizing means for vaporizing the particles of interest output from the solvent removal means to produce vapor for analysis by the detector.

32. An improved interface as defined in claim 23, further comprising:
flow path means having a substantially uniform cross-sectional area for transferring an aerosol including the carrier gas, the vaporized solvent, and the sample particles of interest from the desolvation chamber such that rapid expansion or contraction of the aerosol is minimized, the flow path means having a substantially uniform cross-sectional area for transferring an aerosol including the carrier gas, the vaporized solvent, and the sample particles of interest from the desolvation chamber such that rapid expansion or contraction of the aerosol is minimized.

33. An improved interface as defined in claim 23, further comprising:
a substantially uniform diameter flow tube defining the cross-sectional flow area within the desolvation chamber, the flow path means, and the solvent removal means.

34. An improved method for producing particles of interest for analysis of a sample by a detector from liquid effluent including sample solute and solvent discharged from a liquid chromatographic device, the method comprising;
spraying the liquid effluent into a desolvation chamber;
controllably heating the temperature of the liquid effluent in the desolvation chamber such that substantially all solvent within the desolvation chamber is vaporized while sample particles of interest remain in the desolvation chamber;
inputting a selected carrier gas to the desolvation chamber;
transferring an aerosol including the carrier gas, the vaporized solvent, and the particles of interest from the desolvation chamber;
providing a gas diffusion membrane separating the aerosol from an adjoining secondary flow chamber; and
diffusing solvent from the aerosol to the secondary flow chamber for continuously removing solvent from the transferred aerosol while outputting the carrier gas and sample particles of interest for analysis by the detector.

35. The method as defined in claim 34, wherein the liquid effluent is supplied to the desolvation chamber continuously while liquid effluent including sample solute over a range of atomic mass units is continually supplied to the interface from the liquid chromatographic device.

36. An improved method as defined in claim 34, wherein the carrier gas is selected as a function of the detector.

37. An improved method as defined in claim 34, wherein the carrier gas is selected such that the detector is substantially non-responsive to the carrier gas.

38. An improved method as defined in claim 34, further comprising:
adding a selected solvent to the liquid effluent being sprayed into the desolvation chamber which is more volatile than the solvent in the liquid effluent.

39. An improved method as defined in claim 34, further comprising:
heating the liquid effluent prior to being discharged into the desolvation chamber; and
vaporizing a substantial portion of the solvent from the liquid chromatographic device prior to being discharged into the desolvation chamber.

40. An improved method as defined in claim 34, further comprising
cooling the aerosol to condense the solvent vapor into liquid solvent; and
removing the condensed liquid solvent while outputting the carrier gas and the sample particles of interest to the detector.

41. An improved method as defined in claim 40, further comprising:
providing a liquid waste drain for continuously outputting the condensed liquid solvent; and
substantially all condensed liquid vapor flows through a portion of a flow path to the liquid waste drain in a counterflow direction to the flow of aerosol through the portion of the flow path.

42. An improved method as defined in claim 40, further comprising:
cooling the aerosol at respective first and second serially spaced locations within a condenser; and
providing a transition section between the first and second serially spaced locations for revaporizing condensed solvent carried on the particles of interest past the first location and recondensing the solvent off said particles of interest at the second location.

43. An improved method as defined in claim 34, further comprising:
providing a substantially uniform diameter flow tube for defining the cross-sectional flow area within the desolvation chamber.

44. An improved method as defined in claim 34, further comprising:
regulating carrier gas flow rate into the desolvation chamber such that the carrier gas flow rate is greater than the flow rate of vapor discharged into the desolvation chamber.

45. An improved method as defined in claim 34, further comprising:
positioning a discharge end of a sprayer within the desolvation chamber; and
inputting the carrier gas within the desolvation chamber circumferentially about the discharge end of the sprayer such that the carrier gas within the desolvation chamber flows axially toward the discharge end of the sprayer.

46. An improved method as defined in claim 34, further comprising:
providing a cyrogenic trap for collecting in solid form at least substantially all remaining solvent vapor such that substantially only carrier gas and particles of interest are passed to the detector.

47. An improved method as defined in claim 34, further comprising:
the detector is a gas phase detector; and
vaporizing the particles of interest to produce vapor for analysis by the gas phase detector.

48. An improved method as defined in claim 34, further comprising:
inputting a selected liquid solvent to the liquid effluent discharged into the desolvation chamber, the selected liquid having a lower volatility than the liquid effluent solvent to control particle size of the particles of interest within the desolvation chamber.

49. An improved method as defined in claim 34, further comprising:
maintaining the desolvation chamber at substantially atmospheric pressure while the liquid effluent is sprayed into the desolvation chamber.

50. An improved method as defined in claim 34, further comprising:
regulating the flow of carrier gas to the desolvation chamber such that vaporized solvent and the carrier gas flow at laminar flow rates through a flow path prior to removal of the solvent.

51. An improved method as defined in claim 34, further comprising:
sensing the temperature of the solvent vapor within the desolvation chamber and generating a signal to control the heating of the liquid effluent within the desolvation chamber to response thereto.

52. An improved method as defined in claim 34, further comprising:

moving a collection surface; and depositing the particles of interest on the collection surface for analysis by the detector.

53. An improved method as defined in claim 52, wherein:

regulating the distance between a nozzle and an axially spaced skimmer for controllably removing carrier gas from the particles of interest; and the detector is an electron impact mass spectrometer.

54. An improved method as defined in claim 34, further comprising:

adding reagent gas to the carrier gas input to the desolvation chamber; and the detector is a chemical ionization mass spectrometer.

* * * * *

UNITED STATES PATENT AND TRADEMARK OFFICE
CERTIFICATE OF CORRECTION

PATENT NO. : 4,883,958

DATED : November 28, 1989

INVENTOR(S) : Marvin L. Vestal

It is certified that error appears in the above-identified patent and that said Letters Patent is hereby corrected as shown below:

In Column 6, between lines 33 and 34, insert the following equation $$-- Z = \frac{Pv(T) - Pa}{(2\pi mkT)^{1/2}} \quad \text{Equation 1} --$$

In Column 6, between lines 39 and 40, insert the following equation $$-- V_v = \frac{Pv(T) - Pa}{\rho L} \left(\frac{m}{2\pi kT}\right)^{1/2} \quad \text{Equation 2} --$$

In Column 6, between lines 55 and 56, insert the following equation $$-- N_d = \frac{10^{11}}{\pi} \left(\frac{F(1-f)}{d^3}\right) \quad \text{Equation 3} --$$

In Column 6, between lines 60 and 61, insert the following equation $$-- \frac{dr}{dt} = -V_v \quad \text{Equation 4} --$$

UNITED STATES PATENT AND TRADEMARK OFFICE
CERTIFICATE OF CORRECTION

PATENT NO. : 4,883,958

DATED : November 28, 1989

INVENTOR(S) : Marvin L. Vestal

It is certified that error appears in the above-identified patent and that said Letters Patent is hereby corrected as shown below:

In Column 16, line 37, delete "heated".

In Column 17, line 35, delete "the solvent" and insert therefor --solvent--.

In Column 20, line 1, delete "surface" and insert therefor --interface--.

In Column 21, line 59, after "comprising" insert therefor --:--.

Signed and Sealed this

Twentieth Day of November, 1990

*Attest:*

HARRY F. MANBECK, JR.

*Attesting Officer*    *Commissioner of Patents and Trademarks*